(12) United States Patent
Jackson et al.

(10) Patent No.: US 10,183,238 B2
(45) Date of Patent: Jan. 22, 2019

(54) FLOW SPLITTING IN SUPERCRITICAL FLUID CHROMATOGRAPHY SYSTEMS

(71) Applicant: Waters Technologies Corporation, Milford, MA (US)

(72) Inventors: Michael R. Jackson, Woonsocket, RI (US); James E. Usowicz, Webster, MA (US); Lucas O. Tiziani, Seekonk, MA (US); Joseph A. Jarrell, Newton Highlands, MA (US); Douglas P. Wittmer, Shrewsbury, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 723 days.

(21) Appl. No.: 14/383,241

(22) PCT Filed: Mar. 5, 2013

(86) PCT No.: PCT/US2013/029049
§ 371 (c)(1),
(2) Date: Sep. 5, 2014

(87) PCT Pub. No.: WO2013/134223
PCT Pub. Date: Sep. 12, 2013

(65) Prior Publication Data
US 2015/0021265 A1    Jan. 22, 2015

Related U.S. Application Data

(60) Provisional application No. 61/608,143, filed on Mar. 8, 2012.

(51) Int. Cl.
*B01D 15/08*   (2006.01)
*B01D 15/14*   (2006.01)
(Continued)

(52) U.S. Cl.
CPC ............ *B01D 15/40* (2013.01); *B01D 15/08* (2013.01); *B01D 15/14* (2013.01); *F04B 15/08* (2013.01);
(Continued)

(58) Field of Classification Search
CPC .......... F04B 53/10; F04B 15/08; B01D 15/40; B01D 15/08; B01D 15/14; G01N 30/38;
(Continued)

(56) References Cited

U.S. PATENT DOCUMENTS 5,108,466 A    4/1992   Klein et al.
5,472,612 A *  12/1995  Maxwell ............ B01D 11/0203
                                                      210/181

(Continued)

FOREIGN PATENT DOCUMENTS

WO   WO 2010118414 A1 *  10/2010  ............. G01N 24/08
WO       2011085353         7/2011

OTHER PUBLICATIONS

Zeng, L., et al., "Parallel supercritical fluid chromatography/mass spectrometry system for high-throughput enantioselective optimization and separation," 1169, 193-204 (2007).*

Engell, S., et al., "Optimisation and control of chromatography", Computers and Chemical Engineering, 29, pp. 1243-1252 (2005).*

Zeng, L., et al., "Parallel supercritical fluid chromatography/mass spectrometry system for high-throughput enantioselective optimization and separation", Journal of Chromatography A, 1169, pp. 193-204 (2007).*

(Continued)

*Primary Examiner* — Katherine Zalasky
*Assistant Examiner* — Benjamin L Lebron
(74) *Attorney, Agent, or Firm* — Schmeiser, Olsen & Watts LLP

(57) ABSTRACT

A method includes passing a mobile phase fluid flow comprising liquefied $CO_2$ through a separation column; then introducing a makeup fluid flow into the mobile phase fluid flow to form a mixed fluid flow; and then splitting the mixed fluid flow.

9 Claims, 4 Drawing Sheets

(51) Int. Cl.
*B01D 15/40* (2006.01)
*F04B 15/08* (2006.01)
*G01N 1/40* (2006.01)
*G01N 30/10* (2006.01)
*G01N 30/38* (2006.01)
*G01N 30/72* (2006.01)
*G01N 30/74* (2006.01)
*G01N 30/88* (2006.01)
*H01J 49/04* (2006.01)
*G01N 30/02* (2006.01)
*F04B 53/10* (2006.01)
*G01N 30/24* (2006.01)

(52) U.S. Cl.
CPC ............... *G01N 1/40* (2013.01); *G01N 1/405* (2013.01); *G01N 30/02* (2013.01); *G01N 30/10* (2013.01); *G01N 30/38* (2013.01); *G01N 30/7233* (2013.01); *G01N 30/74* (2013.01); *F04B 53/10* (2013.01); *G01N 30/24* (2013.01); *G01N 30/72* (2013.01); *G01N 2030/8813* (2013.01); *H01J 49/04* (2013.01)

(58) Field of Classification Search
CPC ........... G01N 30/72; G01N 2030/8813; G01N 30/02; G01N 30/10; G01N 30/24; G01N 30/74; G01N 30/7233; G01N 1/40; G01N 1/405
See application file for complete search history.

(56) References Cited

U.S. PATENT DOCUMENTS

| | | | |
|---|---|---|---|
| 5,584,989 A * | 12/1996 | Jameson | B01D 11/0203 210/137 |
| 6,071,408 A | 6/2000 | Allington et al. | |
| 6,360,589 B1 | 3/2002 | Kanda et al. | |
| 2002/0185442 A1* | 12/2002 | Maiefski | B01D 15/08 210/656 |
| 2004/0026617 A1 | 2/2004 | Gregori et al. | |
| 2004/0026661 A1 | 2/2004 | Gregori et al. | |
| 2004/0217273 A1 | 11/2004 | Bai et al. | |
| 2009/0165873 A1* | 7/2009 | Chordia | G01N 30/84 137/597 |
| 2011/0306146 A1 | 12/2011 | Sidhu et al. | |

OTHER PUBLICATIONS

Hirata, Y., et al., "Control of flow rate in supercritical fluid chromatography", Chromatographia, vol. 21, No. 11, pp. 627-630 (1986).*
International Search Report for Application No. PCT/US13/29049, dated May 20, 2013, 4 pages.
International Written Opinion Report for Application No. PCT/US13/29049, dated May 20, 2013, 5 page.
Naegele, E., et al., "Analysis of pesticides in vegetables using the Agilent 1260 Infinity Analytical SFC system with triple quadrupole MS detection," Application Note, Agilent Technologies, Inc., Waldbronn, Germany; published Feb. 1, 2015; pp. 1-8.

* cited by examiner

FLOW SPLITTING IN SUPERCRITICAL FLUID CHROMATOGRAPHY SYSTEMS

RELATED APPLICATIONS

This application is the National Stage of International Application No. PCT/US2013/029049, filed on Mar. 5, 2013, which claims priority to and benefit of U.S. Provisional Patent Application No. 61/608,143 entitled "Flow Splitting in Supercritical Fluid Chromatography Systems," filed Mar. 8, 2012. The contents and teachings of each of these applications are hereby expressly incorporated herein by reference in their entirety.

TECHNICAL FIELD

This disclosure relates to flow splitting in supercritical fluid chromatography, and, in one particular implementation, to a supercritical fluid chromatography system with a pre-split makeup fluid flow.

BACKGROUND

Supercritical fluid chromatography (SFC) is a chromatographic separation technique that typically utilizes liquefied carbon dioxide ($CO_2$) as a mobile phase solvent. In order to keep the mobile phase in liquid (or liquid-like density) form, the chromatographic flow path is pressurized; typically to a pressure of at least 1100 psi.

SUMMARY

This disclosure is based, in part, on the realization that a makeup fluid flow can be introduced into a supercritical fluid chromatography system in a position upstream of a flow splitter. The pre-split makeup fluid flow can help to allow a back pressure regulator to operate in a stable manner while splitting flow from the system (e.g., so that a portion of the flow can be sent to a destructive detector such as a mass spectrometer).

One implementation features a method that includes passing a mobile phase fluid flow comprising liquefied $CO_2$ through a separation column; then introducing a makeup fluid flow into the mobile phase fluid flow to form a mixed fluid flow; and then splitting the mixed fluid flow.

Another implementation provides a supercritical fluid chromatography (SFC) system that includes a separation column, a flow splitter in fluidic communication with the separation column, a makeup pump (e.g., a positive displacement pump) for introducing a makeup fluid flow into the system, and a mixing tee that is arranged in a position downstream of the separation column and upstream of the flow splitter. The mixing tee is configured to mix the makeup fluid flow with a mobile phase fluid flow from the separation column to form a mixed fluid flow. The flow splitter is configured to receive the mixed fluid flow from the mixing tee and split the mixed fluid flow.

Implementations can include one or more of the following features.

In some implementations, splitting the mixed fluid flow includes diverting a first portion of the mixed fluid flow toward a back pressure regulator.

In certain implementations, splitting the mixed fluid flow also includes diverting a second portion of the mixed fluid flow toward a destructive detector.

In some implementations, the step of diverting a second portion of the mixed fluid flow toward a destructive detector comprises diverting a second portion of the mixed fluid flow toward a mass spectrometer.

In certain implementations, the makeup fluid flow includes a fluid that exists in liquid phase at ambient temperature and pressure.

The makeup fluid flow can be methanol.

In some implementations, the mobile phase fluid flow is passed through a non-destructive detector after it is passed through the separation column, and before the makeup fluid flow is introduced into the mobile phase fluid flow.

In certain implementations, the separation column has an inner diameter of 10 mm or less (e.g., 5 mm or less, e.g., 2.1 mm).

In some implementations, the SFC system also includes a back pressure regulator in fluidic communication with the flow splitter. The flow splitter is arranged to deliver a first portion of the mixed fluid flow toward the back pressure regulator.

In certain implementations, the SFC system also includes a destructive detector (e.g., a mass spectrometer) in fluidic communication with the flow splitter. The flow splitter is arranged to deliver a second portion of the mixed fluid flow toward the destructive detector.

In some implementations, the SFC system also includes a makeup fluid source in fluidic communication with the makeup pump.

In certain implementations, the SFC system also includes at least one mobile phase pump configured to deliver the mobile phase fluid flow comprising liquefied $CO_2$ toward the separation column.

In some implementations, the SFC system also includes a carbon dioxide source in fluidic communication with the at least one mobile phase pump.

In certain implementations, the SFC system also includes an inject valve configured to introduce a sample plug into the mobile phase fluid flow.

Implementations can provide one or more of the following advantages.

In some implementations, a pre-split makeup fluid flow introduction allows a back pressure regulator to stay stabilized at an elevated pressure even with very low system or main pump flow.

In certain implementations, a pre-split makeup fluid flow introduction allows use of an entire operating envelope of a system. This can be particularly beneficial when high resistive columns are used in an SFC system.

Other aspects, features, and advantages are in the description, drawings, and claims.

BRIEF DESCRIPTION OF THE DRAWINGS

Like reference numbers indicate like elements.

DETAILED DESCRIPTION

System Overview

Figure 1:
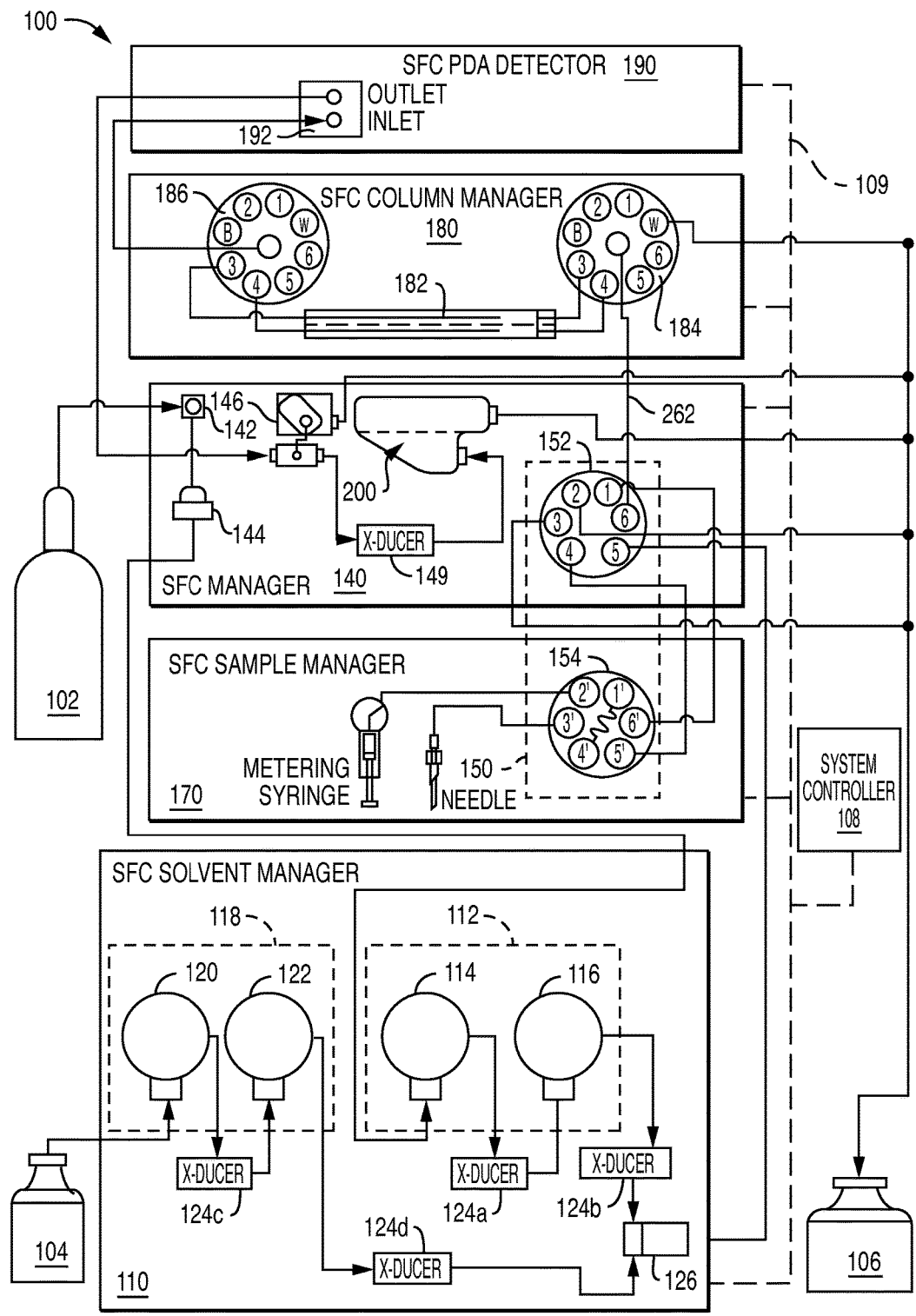
FIG. 1 is a schematic view of a supercritical fluid chromatography (SFC) system.

FIG. 1 schematically depicts a supercritical fluid chromatography (SFC) system 100. The SFC system 100 includes a plurality of stackable modules including a solvent manager 110; an SFC manager 140; a sample manager 170; a column manager 180; and a detector module 190.

The solvent manager 110 is comprised of a first pump 112 which receives carbon dioxide ($CO_2$) from $CO_2$ source 102 (e.g., a tank containing compressed $CO_2$). The $CO_2$ passes through an inlet shutoff valve 142 and a filter 144 in the SFC manager 140 on its way to the first pump 112. The first pump 112 can comprise one or more actuators each comprising or connected to cooling means, such as a cooling coil and/or a thermoelectric cooler, for cooling the flow of $CO_2$ as it passes through the first pump 112 to help ensure that the $CO_2$ fluid flow is deliverable in liquid form. In some cases, the first pump 112 comprises a primary actuator 114 and an accumulator actuator 116. The primary and accumulator actuators 114, 116 each include an associated pump head, and are connected in series. The accumulator actuator 116 delivers $CO_2$ to the system 100. The primary actuator 114 delivers $CO_2$ to the system 100 while refilling the accumulator actuator 116.

In some cases, the solvent manager 110 also includes a second pump 118 for receiving an organic co-solvent (e.g., methanol, water ($H_2O$), etc.) from a co-solvent source 104 and delivering it to the system 110. The second pump 118 can comprise a primary actuator 120 and an accumulator actuator 122, each including an associated pump head. The primary and accumulator actuators 120, 122 of the second pump 118 are connected in series. The accumulator actuator 122 delivers co-solvent to the system 100. The primary actuator 120 delivers co-solvent to the system 100 while refilling the accumulator actuator 122.

Transducers 124a-d are connected to outlets of the respective pump heads for monitoring pressure. The solvent manager 110 also includes electrical drives for driving the primary actuators 114, 120 and the accumulator actuators 116, 122. The $CO_2$ and co-solvent fluid flows from the first and second pumps 112, 118, respectively, and are mixed at a tee 126 forming a mobile phase fluid flow that continues to an injection valve subsystem 200, which injects a sample slug for separation into the mobile phase fluid flow.

In the illustrated example, the injection valve subsystem 150 is comprised of an auxiliary valve 152 that is disposed in the SFC manager 140 and an inject valve 154 that is disposed in the sample manager 170. The auxiliary valve 152 and the inject valve 152 are fluidically connected and the operations of these two valves are coordinated to introduce a sample plug into the mobile phase fluid flow. The inject valve 154 is operable to draw up a sample plug from a sample source (e.g., a vial) in the sample manager 170 and the auxiliary valve 152 is operable to control the flow of mobile phase fluid into and out of the inject valve 154. The SFC manager 140 also includes a valve actuator for actuating the auxiliary valve 152 and electrical drives for driving the valve actuations. Similarly, the sample manager 170 includes a valve actuator for actuating the inject valve 154 and electrical drives for driving the valve actuations.

From the injection valve subsystem 150, the mobile phase fluid flow containing the injected sample plug continues through a separation column 182 in the column manager 180, where the sample plug is separated into its individual component parts. The column manager 180 comprises a plurality of such separation columns, and inlet and outlet switching valves 184, 186 for switching between the various separation columns.

After passing through the separation column 182, the mobile phase fluid flow continues on to a detector 192 (e.g., a flow cell/photodiode array type detector) housed within the detector module 190 then through a vent valve 146 and then on to a back pressure regulator 148 in the SFC manager 140 before being exhausted to waste 106. A transducer 149 is provided between the vent valve 146 and the back pressure regulator 148.

The back pressure regulator 148 is adjustable to control or modify the system fluid pressure. This can allow the pressure to be changed from run to run. The properties of $CO_2$ affect how quickly compounds are extracted from the separation column 182, so the ability to change the pressure can allow for different separation based on pressure. Generally, the back pressure regulator 148 can be used to maintain the system pressure in the range of about 1500 psi to about 6000 psi.

Also shown schematically in FIG. 1 is a computerized system controller 108 that can assist in coordinating operation of the SFC system 100. Each of the individual modules 110, 140, 170, 180, 190 also includes its own control electronics, which can interface with each other and with the system controller 108 via an Ethernet connection 109. The control electronics for each module can include non-volatile memory with computer-readable instructions (firmware) for controlling operation of the respective module's components (e.g., the pumps, valves, etc.) in response to signals received from the system controller 108 or from the other modules. Each module's control electronics can also include at least one processor for executing the computer-readable instructions, receiving input, and sending output. The control electronics can also include one or more digital-to-analog (D/A) converters for converting digital output from one of the processors to an analog signal for actuating an associated one of the pumps or valves (e.g., via an associated pump or valve actuator). The control electronics can also include one or more analog-to-digital (A/D) converters for converting an analog signal, such as from system sensors (e.g., pressure transducers), to a digital signal for input to one of the processors. In some cases, some or all of the various features of these control electronics can be integrated in a microcontroller.

Makeup Fluid Flow

In some instances it may be desirable to split the mobile phase fluid flow after it exits the separation column 182. For example, it may be desirable to deliver analyte molecules carried in the mobile phase fluid flow to a destructive detector (e.g., a mass spectrometer) while continuing to provide a portion of the mobile phase fluid flow to the back pressure regulator 148 in order to regulate system pressure.

Figure 2:
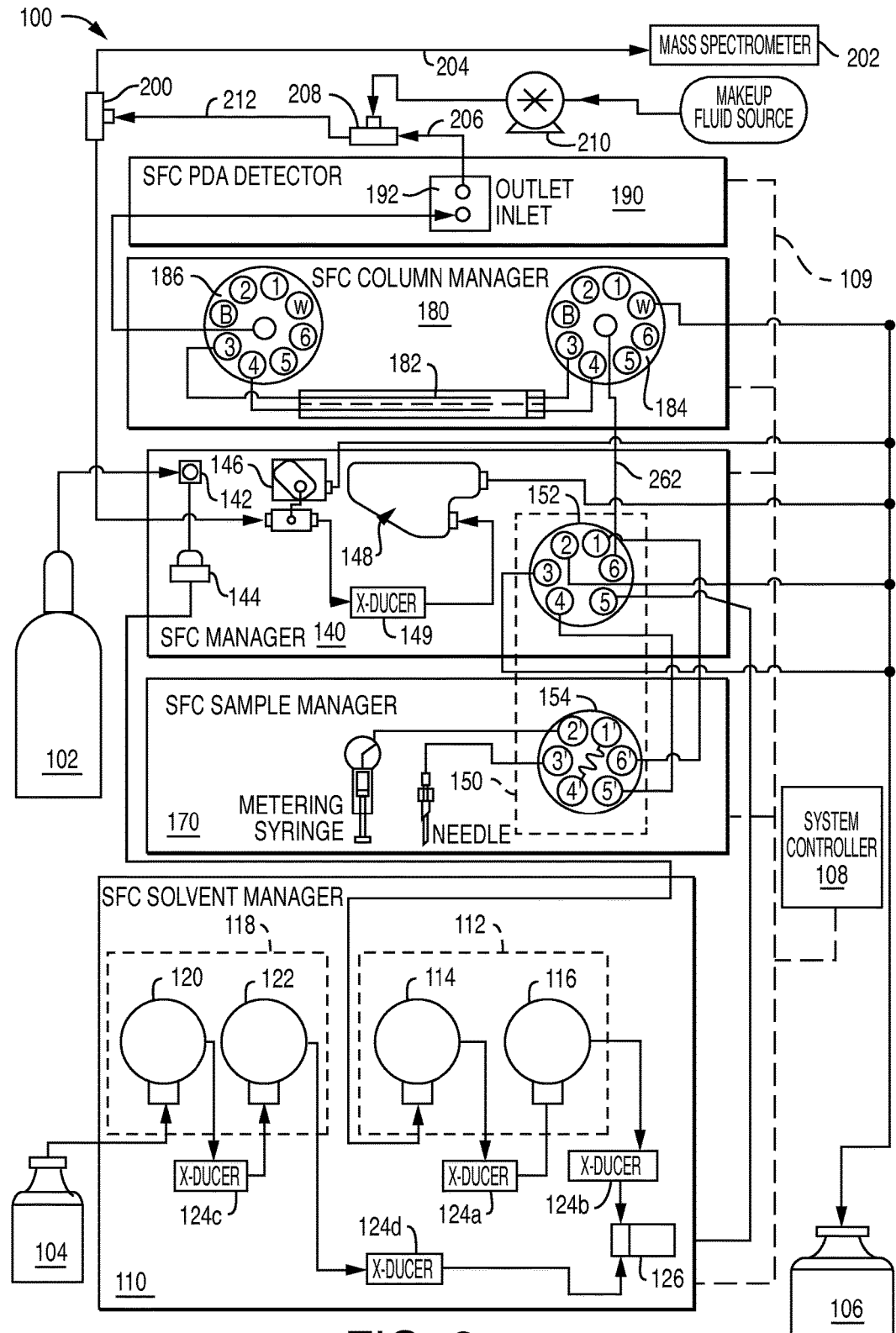
FIG. 2 is a schematic view of a modified version of the SFC system of FIG. 1 which includes the addition of a flow splitter for the purpose of delivering a portion of a mobile phase fluid flow to a mass spectrometer.

FIG. 2 illustrates an implementation of the system 100 which utilizes a flow splitter 200 for the purpose of delivering a portion of the mobile phase fluid flow to a mass spectrometer 202. The solvent manager and sample manager are not shown in FIG. 2, and additional details of the other modules and of the system in have been removed from FIG. 2 to simplify the figure. The portion of the mobile phase fluid flow that is delivered to the mass spectrometer is exposed to atmospheric pressure. As a result, the $CO_2$ in that portion of the mobile phase fluid flow will experience a change to gas phase which can cause tubing 204 to freeze, and/or may cause the sample analytes to come out of the evaporating mobile phase solution and attach to the wall of the tubing 204 (e.g., a 30 inch long section of 0.002 inch inner diameter PEEKsil™ tubing available from SGE Analytical Science, Ringwood, Victoria, Australia). In this regard, a makeup fluid flow can be provided to help manage the phase change, to help keep the sample analytes in solution, and to allow a liquid stream to be delivered the mass spectrometer. The makeup fluid can be methanol, or another solvent that exists in liquid phase at ambient temperature and pressure.

As illustrated in FIG. 2, the mobile phase fluid flow exits an outlet of the detector 192, a non-destructive detector, and is delivered via tubing 206 (e.g., a 6 inch long section of 0.007 inch inner diameter polyether-ether-ketone tubing) to a mixing tee 208 where it merges with the makeup fluid flow provided from makeup pump 210 (e.g., a positive displacement pump). The mixed fluid flow is then delivered to the flow splitter 200 via tubing 212 (e.g., a 6 inch long section of 0.007 inch inner diameter polyether-ether-ketone tubing) where the mixed fluid flow is split. A first portion of the mixed fluid flow is delivered toward the back pressure regulator 148 and a second portion of the mixed fluid flow is delivered toward the mass spectrometer 202.

Advantageously, the makeup fluid flow is introduced into the mobile phase fluid flow in a region upstream of the flow splitter 200. This provides flow to the back pressure regulator 148 allowing the back pressure regulator 148 to stay stabilized at an elevated pressure even with very low main pump flow. That is, the splitting of the flow introduces what amounts to a leak in the system 100, and the introduction of the makeup fluid flow upstream of the split helps to compensate for this loss of fluid flow to the back pressure regulator 148. As the flow rate ($Q_{MUP}$) of the makeup fluid flow increases the flow rate ($Q_{BPR}$) of the portion of the mixed fluid flow that is delivered to the back pressure regulator 148 increases and the flow rate ($Q_{Split}$) of the portion of the mixed fluid flow that is delivered to the mass spectrometer 202 stays the same. the flow rate ($Q_{MUP}$) of the makeup fluid flow can increase as long as the back pressure regulator 148 can hold pressure at the new flow rate. The flow rate ($Q_{Split}$) of the portion of the mixed fluid flow that is delivered to the mass spectrometer 202 will never be zero. And, as long as $Q_{MUP}$ is equal to $Q_{split}$ the back pressure regulator 148 will never be starved.

In addition, the introduction of the makeup fluid flow upstream of the flow splitter 200 allows for the use of the entire flow envelope of the system 100. This can be particularly beneficial when highly restrictive separation columns are used in the system 100. This benefit is illustrated graphically in FIGS. 3A and 3B.

Figure 3A:
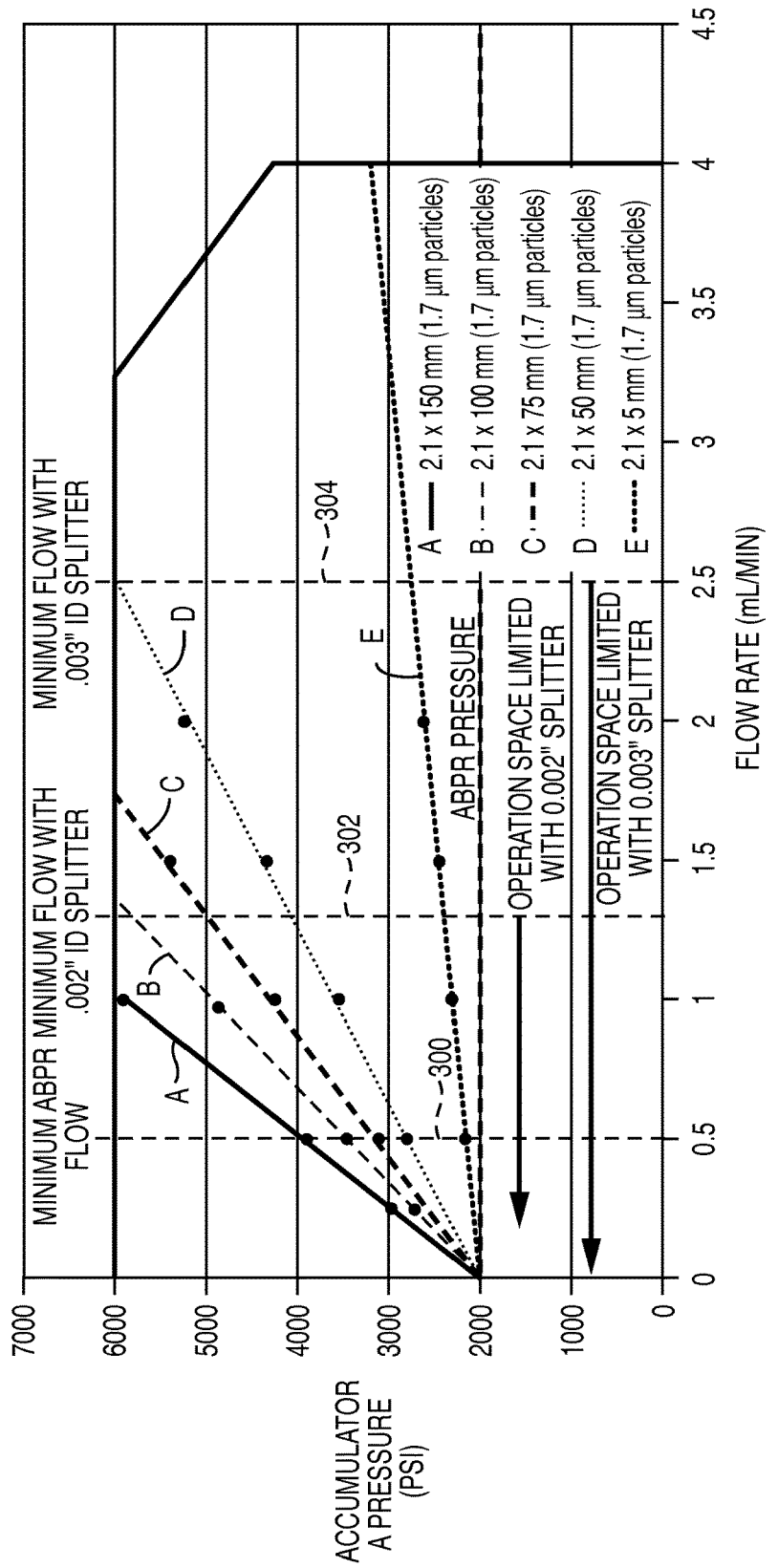
FIG. 3A is a graphical depiction of a constrained operating envelope that one would have with a post-split makeup fluid flow introduction.

FIG. 3A graphically depicts an operating envelope for the accumulator actuator 116 along with operating curves for highly restrictive, 2.1 mm inner diameter (ID) columns of various lengths. FIG. 3A shows a constrained flow rate envelope that one would have with a post-split makeup fluid flow introduction (i.e., introduction of makeup fluid flow downstream of the flow splitter 200). As shown in FIG. 3A, the first pump 112 has a maximum operating pressure of 6000 psi and a maximum flow rate of 4 ml/min. Where there is no flow splitting and no makeup fluid flow, the accumulator actuator 116 must provide a minimum flow rate of 0.5 mL/min in order for the back pressure regulator 148 to stabilize system fluid pressure to 2000 psi, as indicated by line 300.

Line 302 indicates the minimum flow rate (about 1.4 mL/min) that the accumulator actuator 116 must provide in order for the back pressure regulator 148 to stabilize system fluid pressure to 2000 psi in the situation in which the mobile phase fluid flow is split with a 0.002 inch inner diameter flow splitter. As shown in FIG. 3A, the operating ranges of the 150 mm, 100 mm, and 75 mm columns are almost entirely outside of the reduced flow envelope.

The operating envelope is further reduced when a 0.003 inch inner diameter flow splitter is used. In this case, the accumulator actuator 116 must provide a minimum flow rate of about 2.5 mL/min (line 304) in order for the back pressure regulator 148 to stabilize system fluid pressure to 2000 psi. As shown in FIG. 3, where a 0.003 inch inner diameter flow splitter is used, the operating ranges of the 150 mm, 100 mm, 75 mm, and the 50 mm columns are outside of the reduced flow envelope, thereby limiting the columns that can be used with such a configuration.

Figure 3B:
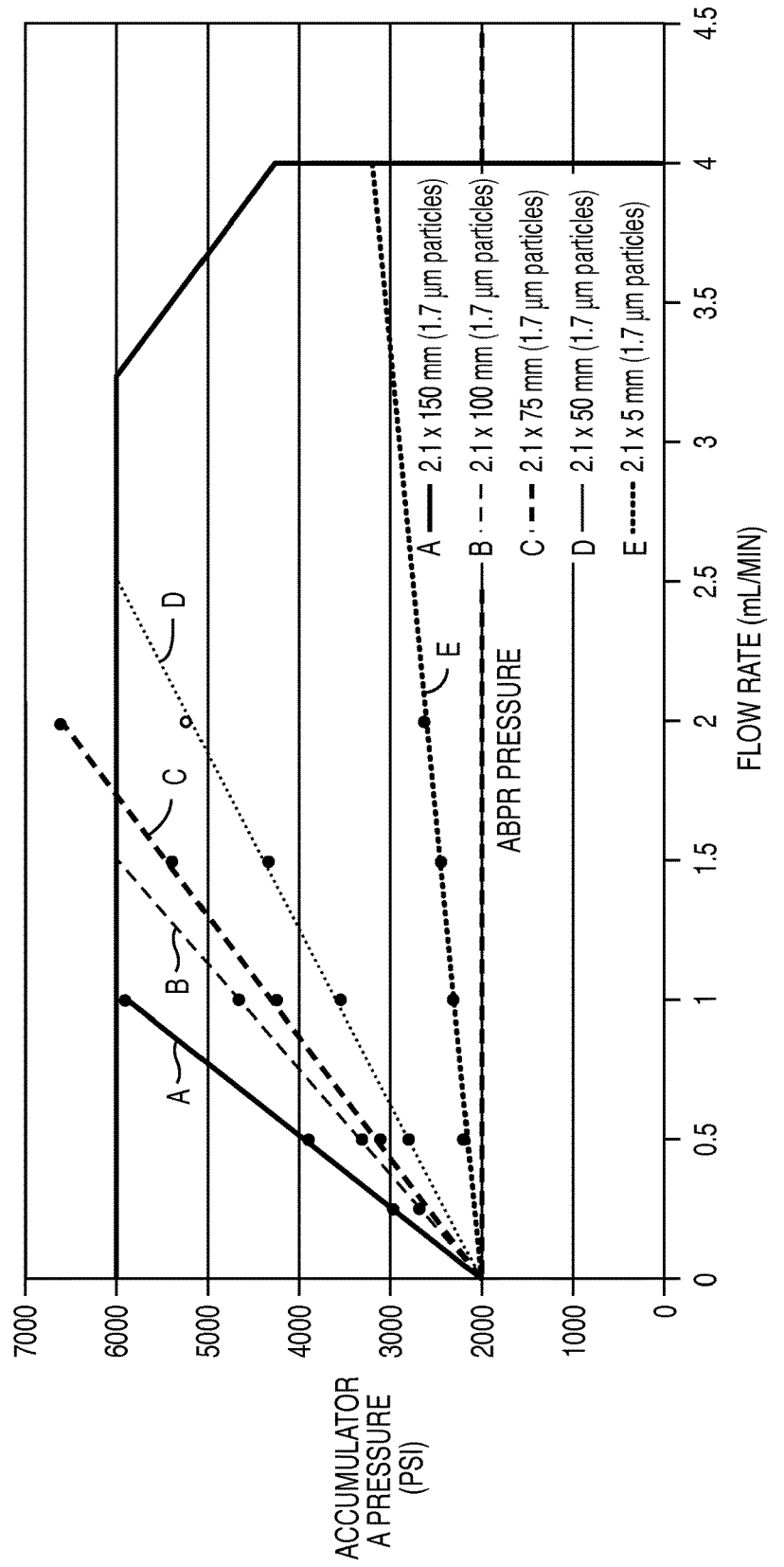
FIG. 3B is a graphical depiction of an operating envelope that one has with pre-split makeup fluid flow introduction.

FIG. 3B shows the operating envelope that one has with pre-split makeup fluid flow introduction (i.e., introduction of makeup fluid flow upstream of the flow splitter 200). As shown in FIG. 3B, in the pre-split configuration the makeup pump 210 can deliver the flow to the system to allow the back pressure regulator 148 to control the system pressure and the flow limitation on the accumulator actuator 116 can be removed thereby opening up the entire operating envelope. As FIG. 3B illustrates, this pre-split makeup fluid flow introduction allows for the use of highly resistive columns.

Other Implementations

Although a few implementations have been described in detail above, other modifications are possible. For example, while an implementation has been described in which the mobile phase fluid flow passes through a non-destructive detector before the makeup fluid flow is introduced, in some cases, the mobile phase fluid flow may pass directly from the outlet of a separation column to the mixing tee so that the makeup fluid flow is introduced into the mobile phase fluid flow without having the mobile phase fluid flow pass through a nondestructive detector first.

Accordingly, other implementations are within the scope of the following claims.

What is claimed is:
1. A method comprising:
   passing a mobile phase fluid flow comprising liquefied CO2 through a separation column; then
   introducing a makeup fluid flow into the mobile phase fluid flow to form a mixed fluid flow upstream of a flow splitter; then
   splitting the mixed fluid flow at the flow splitter to simultaneously divert a first portion of the mixed fluid flow toward a back pressure regulator and a second portion of the mixed fluid flow toward a destructive detector;
   wherein the first portion of the mixed fluid flow enables the back pressure regulator to stabilize a system fluid pressure by compensating for loss of fluid flow to the back pressure regulator as a result of the splitting; and
   controlling a flow rate of the makeup fluid flow to at least equal a flow rate of the second portion of the mixed fluid flow.

2. The method of claim 1, wherein diverting a second portion of the mixed fluid flow toward a destructive detector comprises diverting a second portion of the mixed fluid flow toward a mass spectrometer.

3. The method of claim 1, wherein the makeup fluid flow comprises a fluid that exits exists in liquid phase at ambient temperature and pressure.

4. The method claim 3, wherein the makeup fluid flow comprises methanol.

5. The method of claim 1, further comprising passing the mobile phase fluid flow through a non-destructive detector after passing the mobile phase fluid flow through the separation column, and before introducing the makeup fluid flow into the mobile phase fluid flow.

6. The method of claim 1, wherein the separation column has an inner diameter in the range of about 10 mm to about 5 mm or less than about 5 mm.

7. The method of claim 1, further comprising passing the mobile phase fluid flow through a non-destructive detector after introducing the makeup fluid flow into the mobile phase fluid flow.

8. The method of claim 1, further comprising passing the mixed fluid flow through a vent valve before the back pressure regulator.

9. The method of claim 8, further comprising passing the mixed fluid flow through a transducer after the vent valve and before the back pressure regulator.

\* \* \* \* \*